US005879933A

United States Patent [19]
Hodgson

[11] Patent Number: 5,879,933
[45] Date of Patent: Mar. 9, 1999

[54] MAMMALIAN RETROTRANSPOSONS

[75] Inventor: Clague P. Hodgson, Wooster, Ohio

[73] Assignee: Nature Technology Corporation, Omaha, Nebr.

[21] Appl. No.: 269,031

[22] Filed: Jun. 30, 1994

Related U.S. Application Data

[63] Continuation of Ser. No. 968,259, Oct. 29, 1992, Pat. No. 5,354,674, which is a continuation of Ser. No. 603,635, Oct. 25, 1990, abandoned.

[51] Int. Cl.$^6$ ............................. C12N 5/00; C12N 15/00
[52] U.S. Cl. ........................ 435/320.1; 435/325; 935/70
[58] Field of Search ...................... 514/2, 44; 435/172.3, 435/320.1, 325, 240.1, 240.2; 424/93.21; 935/70

[56] References Cited

U.S. PATENT DOCUMENTS

| | | | |
|---|---|---|---|
| 4,405,712 | 9/1983 | Woude et al. | 435/5 |
| 4,615,974 | 10/1986 | Kingsman et al. | 435/68 |
| 4,650,764 | 3/1987 | Temin et al. | 435/240 |
| 4,670,388 | 6/1987 | Rubin et al. | 435/172 |
| 4,686,098 | 8/1987 | Kopchick et al. | 435/424 |
| 4,719,177 | 1/1988 | Baltimore et al. | 435/91 |
| 4,828,987 | 5/1989 | Kophick et al. | 435/68 |
| 4,861,719 | 8/1989 | Miller | 435/236 |
| 4,868,116 | 9/1989 | Morgan et al. | 435/240 |
| 4,873,191 | 10/1989 | Wagner et al. | 435/172 |
| 4,898,823 | 2/1990 | Kingsman et al. | 435/172 |
| 4,918,166 | 4/1990 | Kingsman et al. | 530/350 |
| 4,957,865 | 9/1990 | Samarut et al. | 435/235 |
| 4,980,289 | 12/1990 | Temin et al. | 435/235 |
| 5,354,674 | 10/1994 | Hodgson | 435/172.3 |

FOREIGN PATENT DOCUMENTS

| | | |
|---|---|---|
| 3636287 | 4/1988 | Germany . |
| 8808454 | 11/1988 | WIPO . |

OTHER PUBLICATIONS

Muligan (1993) Science 260, 926–932.
Raffo et al (1991)Virolog 184, 277–289.
Marshall, Science, Science, 269, 1995, 1050–1055.
Culver et al., TIG, 10(5), 1994, 174–178.
Miller et al., FASEB. J., 9, 1995, 190–199.
Hodgson, Exp. Opin. Ther. Pat., 5(5), 1995, 459–468.
Chakraborty, A.K. et al. "Synthetic retrotransposon vectors for gene therapy," FASAB Journal 7: 971–977 (1993).
Chakraborly, A.K. et al. "Expression of VL30 vectors in human cells that are targets for gene therapy," Biochem. Biophys. Res. Comm. 209(2) 677–83 (1995).
Kantoff, P. et al. "Expression of human adenosine deaminase in non–human primates after retrovirus–mediated gene transfer," J. Exp Med 166:219–234 (1987).
E. F. Wagner et al., entitled "The Human β–Globin Gene And A Functional Viral Thymidine Kinase Gene In Developing Mice", Proc. Natl. Acad. Sci. USA, 78, No. 8, pp. 5016–5020, (Aug. 1981).

S.A. Rosenberg, M.D., Ph.D., et al., "Gene Transfer Into Humans—Immunotherapy of Patients With Advanced Melanoma, Using Tumor–Infiltrating Lymphocytes Modified By Retroviral Gene Transduction", *The New England Journal of Modicine*, 323, No. 9, pp. 570–578, (Aug. 30, 1990).
J.D. Boeke et al., "A General Method for the Chromosomal Amplification of Genes in Yeast," *Science*, 239, 280 (15 Jan. 1988).
D.N. Foster et al., *Proc. Nat'l Acad. Sci. USA*, 79, 7317–7321 (1982).
D.N. Foster et al., "Isolation of Mouse DNA Segments Containing Epidermal Growth Factor (EGF) Inducible Sequences," *J. Cell Biochem.*, (Suppl.) 6, 285 (1982).
C.P. Giri et al., "Discrete Regions of Sequence Homology Between Cloned Rodent VL30 Genetic Elements and AKV–related MuLV provirus Genomes," *Nucleic Acids Research*, 11, 305 (1983).
C.P. Hodgson et al., "The Long Terminal Repeats and Associated Flanking Sequences of a Mouse Virus–Like Genetic Element," *DNA*, 2, 83 (1983).
C.P. Hodgson et al., "Nucleotide Sequence of Mouse Virus–Like (VL30) Retrotransposon BVL–1," *Nucleic Acids Research*, 18, 673 (1990).
C.P. Hodgson et al., "Structure and Expression of Mouse VL30 Genes," *Molecular and Cellular Biology*, 3, 2221–2231 (Dec. 1983).
C.P. Hodgson et al., "Mouse Retrovirus–Like (VL30) Transposable Element RNA is Abundantly Expressed in PSI-2 Helper Cells, Transferred to Recipient Rat Hepatoma Cells, and Expressed in a Dexamethasone–Inducible Fashion Along with Specifically Vectored Sequences: Complete Structure," *J. Cellu. Biochem.*, 13D, 54 (1989).
C.P. Hodgson et al., "The Long Terminal Repeats and Associated Flanking Sequences of an Integrated Mouse VL30 Gene," *Dissertation Abstracts International*, 44, 700B (1983).
C.P. Hodgson et al., "The Long Terminal Repeats and Associated Flanking Sequences of an Integrated Mouse VL30 Gene," Doctoral Dissertation, University of Minnesota, Feb., 1983.

(List continued on next page.)

Primary Examiner—Deborah Crouch
Attorney, Agent, or Firm—Schwegman, Lundberg, Woessner & Kluth, P.A.

[57] ABSTRACT

A process for the transfer and/or expression of any gene into cells, organisms or species is disclosed. The process involves isolating the gene, introducing the gene into a vector comprised of at least one retrotransposon genetic element to provide a hybrid gene. The hybrid gene is introduced into a donor cell capable of packaging and transmitting the retrotransposon to other cells, organisms or species. The hybrid gene is transferred to a recipient cell wherein the hybrid gene replicates by reverse transcription and is inserted into the recipient cell's genome. The gene is preferably expressed as RNA and/or protein, giving the phenotype of the gene.

9 Claims, 4 Drawing Sheets

OTHER PUBLICATIONS

R. Jaenisch, "Germ Line Integration and Mendelian Transmission of the Exogenous Moloney Leukemia Virus," *Proc. Nat. Acad. Sci. USA*, 73, 1260–1264.

R. Jaenisch et al., "Chromosomal Position and Activation of Retroviral Genomes Inserted into the Germ Line of Mice," *Cell*, 24, 519–529 (May 1981).

Patent Search: Genetic Vectors, Transduction, Genetic Transfection (Oct. 1990) (a copy of a computer generated search was submitted with the PTO 1449 of the parent application).

Rotman et al., *Nucl. Acid Res.*, 14, 645–658 (1986).

P. Singleton et al., Dictionary of Microbiology and Molecular Biology, 753 (1987 ed.).

H.M. Temin, "Retrovirus Variation and Evolution," *Genome*, 31, 17–22 (1989).

R. Jaenisch, "Transgenic Animals", *Science*, vol. 240, pp. 1468–1474, Jun. 1988.

A.D. Miller, "Human Gene Therapy Comes of Age", *Nature*, Vo. 357, pp. 455–460, Jun. 11, 1992.

MAMMALIAN RETROTRANSPOSONS

This application is a continuation of Ser. No. 07/968,259, filed Oct. 29, 1992 now U.S. Pat 5,354,674, issued Oct. 11, 1994 which is a continuation of Ser. No. 07/603,635, filed Oct. 25, 1990, abandoned.

This invention was made with support under the National Institutes of Health Grant No. GM41314. The U.S. Government has certain rights in the invention.

TECHNICAL FIELD

The present invention relates to the field of molecular biology and method of altering the genetic material of a cell or organism. In particular, the invention relates to the use of retrotransposons as vectors suitable for the expression, at various levels, of genetic material. The present invention has a wide variety of applications, for example, in animal and plant breeding and in the understanding and treatment of various genetic and viral diseases.

BACKGROUND ART

Various methods are currently being used in genetic engineering to enable the transfer and expression of genes into the genomes of cells and organisms. Genes have been transferred by incubating cells with DNA, possibly in the presence of chemicals such as polyions or calcium phosphate. Genetic material can also be injected into the nucleus or cytoplasm of cells or zygotes. Other methods include electroporation, liposome mediated gene insertion, asialoglycoprotein gene insertion, particle acceleration and viral transduction.

The use of viruses in the transduction method has been shown to be very efficient when retroviruses are used. Foreign genes are inserted into either a replication defective or replication competent viral vector construct (usually as a plasmid), and are transferred into cells containing all the genes necessary for packaging and replication of the virus. Special cell lines ("helper" or viral packaging cells) have been constructed which enable defective (non-replication competent) viral vectors to be packaged into infectious particles or virions. The vectors themselves do not harbour the necessary genes for replication so that when the vectors infect cells, the vectors replicate using the enzymes in the viral particle to insert themselves into the host genome (chromosomes). The vectors are unable to replicate further because the essential viral genes were (hopefully) left behind in the "helper" cell. This technique has been adopted and approved for the first human gene therapy trials, despite ongoing debate about the safety of such usages.

Transduction by RNA tumor viruses (retroviruses) has special appeal because it can be rapid, efficient, and results in stable integration of a small number of copies (usually 1–2) of genetic information. Unlike transformation, retroviral integration takes place in a precise fashion, usually at an exact position within the viral genome, and insertion can occur at many places within the host cell genome.

Unfortunately, retroviruses are accompanied by adverse pathogenic and oncogenic effects. However, the infectivity of retrovirus vectors can be controlled by using genetically disabled forms in conjunction with helper cells. In order to function effectively as a vector, the portions of necessary genetic information removed from the disabled vector must be provided "in trans" (by another gene, located outside the vector). Many such helper cell lines containing viral functions necessary for packaging, replication, delivery, and reinsertion of replication defective viral vectors have been put into use for the several tumor virus types commonly used. These useful viruses include the disease organisms causing murine leukemia virus (MLV), spleen necrosis virus (SNV), avian leukosis virus (ALV), and reticuloendotheliosis virus (REV). Patents have issued for helper cell lines for MLV and REV (Miller, U.S. Pat. No. 4,861,719; Temin et al., U.S. Pat. No. 4,650,764).

MLV viruses have become the vectors of choice for animal genetic engineering of cells and organisms, because of their compatibility with a wide variety of animal cell types including certain germ cells as well as human cells. MLV was used to insert viral transgenes into the mouse germline, creating a transgenic mouse (Jaenisch et al., Proc. Nat. Acad. Sci. (USA) 73:1260 (1976) and Cell 24:519 (1981)). MLV vector systems have been approved for limited human gene therapy trials despite some of the problems described above.

While retroviruses are becoming important tools for the transfer of genes into cells there are major problems associated with retroviral vectors. One such problem is the ability of disabled viral vector sequences to recombine with either helper viral sequences, or sequences in the cellular genome, yielding infectious viral particles. This problem has been dealt with by removing more viral sequences from vectors, as well as by introducing multiple mutations and rearrangements in helper sequences. Together, these alterations make it more difficult for the vector to revert to replication competency, but may also lower the viral titre or infectivity. However, recombination events are common in retroviruses (Temin, H.M., Genome 31:17–22 (1989)), and hence reversion and recombination persist to be problems.

Another difficulty associated with RNA tumor viruses is that they tend to be oncogenic. Included in this class are the commonly used MLV vectors which cause neoplasms of various sorts by at least two mechanisms: (1) by activating transcription of nearby cellular oncogenes (cancer genes) due at least in part to powerful enhancer-promoter sequences in the viral transcriptional control region, and (2) by recombining with cellular oncogenes, which then become a part of the viral genome, causing rapid oncogenesis that is borne along with the virus.

An additional problem associated with the use of amphotropic (broad host range) vectors such as those being currently proposed for human gene therapy is that the amphotropic vectors might recombine with another retrovirus in the human or animal host, yielding, for example, amphotropic AIDS (AIDS virus able to infect a broad human host range). The possibility theoretically exists for an amphotropic AIDS virus (HIV) arising by recombination or by phenotypic mixing with amphotropic MLV to initiate an epidemic by greatly expanding the range of human cells in which the HIV virus could replicate.

Thus, it is important to assure that non-replication competent MLV vectors used in gene therapy will have a low potential for reversion or pathogenic effects. Ideally, trans-acting viral genes should be completely isolated from vectors, and vectors should be of non-MLV orgin, nonpathogenic, nononcogenic, and bear as little homology to MLVs as possible in order to limit productive recombination which would yield replication competent virus. To be additionally useful for transgenic work, the vectors should be compatible with long-term residence in the genome of the host organism.

The present invention thus relates to the use of natural, mobile cellular genes (retrotransposons) as candidates for gene engineering vectors. Until the present invention, retrotransposons have not been implemented in a practical forum for such uses as animal gene insertion or gene therapy. In contrast, the research is concentrated in other areas. For example, a neomycin phosphotransferase gene as well as the yeast trp1 gene in yeast have been amplified after introduction of the genes in a yeast GAL1-Ty fusion construct (Boeke et al., Science, 239:280–282, 1988). This involved transposition via Ty element-mediated transposition. Others have developed a means for targeting fusion proteins into yeast Ty retrotransposon particles which can then be harvested and presumably used for the production of antibodies, vaccines, protein purification, diagnostics, and the like. See for example, the Adams et al., U.S. Pat. No. 4,918,166. Nonretro transposons (P elements) have also been used for genetic transposition in the fly Drosophila, see for example, the Rubin et al., U.S. Pat. No. 4,670,388. This involves the insertion of DNA material between defined sequences recognized by transposase, inserting the material into a Drosophila germ cell, and causing the transposable element to be affirmatively inserted into the genome of the recipient Drosophila insect so as to become part of the heritable genome of the insect, wherein the element and foreign DNA can function. Mammalian gene transfer and transgenics is discussed in the Wagner et al., U.S. Pat. No. 4,873,191, 1989. This involves introducing exogenous genetic material into a pronucleus of a mammalian zygote by microinjection. The zygote is capable of development into a mammal, and the genetic material includes at least one gene and a control sequence operably associated therewith. Thus, a genetically transformed zygote is obtained. The embryo or zygote is transplanted to a pseudopregnant female and the embryo is allowed to develop to term, wherein the genes are integrated and expressed. This approach is entirely physical and does not involve retrotransposable elements (retrotransposons do not require micro injection). The earliest apparent use of retroviruses to infect the germ line was by Jaenisch et al., Proc. Nat. Acad. Sci. (USA) 73:1260 (1976) and Cell 24:519, (1981). In addition, the Vande Woude et al., U.S. Pat. No. 4,405,712, describes certain vectors derived from Murine leukemia-sarcoma viruses, and the process of transfecting them into cells, selecting phenotype, and then superinfecting cultures in order to obtain replication competent virus with the vectors packaged as pseudotype. These vectors, and the methods described, are quite primitive by todays standards, and do not involve retrotransposon vectors.

Thus, it is clearly advantageous to develop a new, efficient method for the introduction of cellular mobile elements into the genomes of many species. The uses of such method includes, for example, vectors for studies of gene expression in cultured cells, vectors for transgenic organism production and vectors for human gene therapy.

DISCLOSURE OF INVENTION

The present invention relates to a process or procedure for using retrotransposons as vectors in genetic engineering. The retrotransposons or "jumping genes" are cellular movable genetic elements. The retrotransposons are of non-replication competent cellular origin, and are capable of carrying a foreign gene. The retrotransposons can act as parasites of retroviruses, retaining certain classical hallmarks, such as long terminal repeats (LTR), retroviral primer binding sites, and the like. However, the retrotransposons usually do not contain functional retroviral structure genes which would normally be capable of recombining to yield replication competent viruses. Some retrotransposons are examples of so-called "selfish DNA", or genetic information which encodes nothing except the ability to replicate itself. The retrotransposon may do so by utilizing the occasional presence of a retrovirus or a reverse transcriptase within the host cell, efficiently packaging itself within the viral particle, which transports it to the new host genome, where it is expressed again as RNA. Whatever information is encoded within that RNA is potentially transported with the jumping gene.

Transduction of exogenous genetic information into cells or organisms is attained by first placing the exogenous genes and/or their controlling elements into a retrotransposon genetic element (cellular movable genetic element with long terminal repeats). The LTR and flanking region consists of a genetic entity (RNA or DNA) which contains signals necessary for replication, packaging, insertion, and expression of the genetic element in a host cell as a parasite of retroviral gene transduction. The recombinant retrotransposon is then transfected or otherwise introduced into cells providing retroviral (or retrovirus-like) replicative functions, such as virus producing cells, or else so-called helper cells. The retroviral trans functions combine with RNA transcripts made from the DNA copies of the recombinant retrotransposons to form infectious retrotransposon particles or virions. These retrotransposon particles transduced into the new host cell are reverse transcribed into DNA, and are introduced stably into the new host genome, from which RNA transcripts can again be generated from either the retrotransposon transcriptional unit or from inserted internal transcriptional units, directing the expression of useful genes. The introduced genes are unable to replicate further in the absence of helper functions.

The invention can be utilized for gene therapy, gene insertion and expression studies in cell culture, for the generation of transgenic animals, and in other instances where traditional RNA tumor virus vectors may be considered unsafe or undesirable.

BEST MODE OF CARRYING OUT INVENTION

The following definitions of biological and genetic terms will be useful in understanding this invention:

DNA: Deoxyribonucleic acid, the genetic material of cellular chromosomes.

RNA: Ribonucleic acid, the genetic material of the RNA tumor viruses and retrotransposons during part of the life cycle.

DNA sequence: A linear sequence comprised of any combination of the four DNA monomers. The DNA monomers, nucleotides of adenine, guanine, cytosine and thymine, code for genetic information, including coding for an amino acid, a promoter, a control or a gene product. A specific DNA sequence has a known specific function, for example, codes for a particular polypeptide, a particular genetic trait or affects the expression of a particular phenotype.

Gene: The smallest, independently functional unit of genetic material which codes for a protein product or controls or affects transcription and comprises at least one DNA sequence.

Chimera: A hybrid gene produced by recombinant DNA technology.

Genotype: The genetic constitution of a cell or organism.

Phenotype: A collection of morphological, physiological and biochemical traits possessed by a cell or organism that results from the interaction of the genotype and the environment.

Phenotypic expression: The expression of the code of a DNA sequence or sequences which results in the production of a product, for example, a polypeptide or protein, or alters the expression of the zygote's or the organism's natural phenotype.

Chromosome: A fiber or threadlike structure which is completely or partially composed of genetic nucleic acid.

Retrovirus: A virus which requires reverse transcription of RNA into DNA at some point during its life cycle; specifically the retroviridae, or RNA tumor viruses. This family encompasses all viruses containing an RNA genome and RNA-dependent DNA polymerase (reverse transcriptase).

Retrotransposon: A cellular movable genetic element which is dependent upon reverse transcription.

Vector: Usually an agent transmitting a disease or natural genetic information; here restricted to a genetic agent transmitting a foreign gene (DNA or RNA) construct, unless otherwise indicated.

Genome: One set of chromosomes, haploid or diploid, for an agent or organism.

Transduction: Here limited to the transmission of viral, retrotransposon, or exogenous (added) genes (unless otherwise indicated by means of viral particles or viral functions).

Helper Cell Line: In this context, a cell line which has been genetically engineered or which naturally contains genes capable of generation of some or all necessary retroviral trans-acting functions or proteins, such as reverse transcriptase, viral core proteins, envelope glycoproteins, and/or tRNA for priming reverse transcription and the like. Examples of helper cell lines include psi2, PA317.

Replication Competent Retrovirus: A retrovirus which bears all genes necessary for cis and trans functions; complete, able to replicate without additional viral functions.

Non-replication Competent (defective) retrovirus: A retrovirus which requires supplemental functions in order to replicate, or which is unable to replicate by itself. In this context, it usually requires trans-acting functions such as named above.

Transgene: A foreign gene, usually inserted into a vector.

cis-acting element: Genetic element which must be located on the same piece of nucleic acid in order to function, such as transcriptional promoter or enhance elements, primer binding sites and the like.

trans-acting element: Genetic element which need not be located in cis, i.e., that which may be located elsewhere, such as in the cellular genome. Examples of trans elements are the retroviral core protein, polymerase, and envelope glycoprotein genes.

Psi sequences: Sequences of genetic information which encode the packaging functions which enable particles to package and transmit viral or retrotransposon RNA.

The present invention relates to a process for the transfer and expression of any gene in a cell, organism or species using retrotransposons. Retrotransposons are a class of retrovirus-like DNA elements which are found in the genomes of most mammals. Retrotransposons generally maintain a structural similarity to retroviruses which includes essential replicative elements within the DNA [such as long terminal repeats (LTRs) and primer binding sites] but need not include the capacity to produce proteins or particles, observable phenotype, or significant pathology. Some retrotransposons do encode proteins which may be of significance to the cell, or to the replication of the retrotransposon. Retrotransposons replicate and disperse themselves during a retroviral infection, or when endogenous retroviruses or retroviral genes within the host, or host cellular genes such as cellular reverse transcriptase are activated. Some retrotransposons are thus a part of the so-called "selfish DNA" which occupies a significant fraction of the genomes of man and of most species. However, there is a broad spectrum of such elements and some may naturally bear cellular genes, or genes related to retrotransposon function. While retrotransposons are typically compatible with the host, until the present invention retrotransposons have not been recognized or developed as valuable tools for gene transduction.

One class of retrotransposons is mouse VL30. The VL30 genes are a family of disperse, middle repetitive DNA sequences. The VL30 name is derived from the fact that the VL30 elements exhibit "Virus Like" properties and produce a 30 S RNA in a variety of mouse cells. Also, physically similar and genetically related sequences are present in the rat genome.

Mouse VL30 genes are ~5 kilobase cellular genetic elements found at 100–200 copies integrated into the chromosomes of most mus species. The VL30 genes package into and are efficiently transmitted by murine and primate retroviruses. VL30s and other retrotransposons maintain the structural hallmarks of retroviruses, such as long terminal repeats, tRNA primer binding sites, and inverted terminal repeats, which are associated with various aspects of retroviral replication. However, the VL30 retrotransposons bear little nucleotide homology to murine retroviruses such as MLVs, and the two VO30s sequenced appear to bear no long open reading frames. It is therefore less likely that the characterized VL30s would recombine productively with protein encoding regions of MLVs. However, it is also possible that VL30 packaging signals could recombine with those of MLVs, for these signals are apparently essential for efficient packaging of the RNA into the viral particle, and it is in this packaging (or psi) region of the genome, together with a few base pairs at the borders of the LTRs, where the strongest homology between VL30 retrotransposons and MLVs are found. VL30 MLV recombination has been suggested to play a role in the rapid reversion of mutants in which only the "psi", or packaging region, has been deleted.

One of the first helper cell lines constructed for MLV vectors, psi2, is such a recombination-prone mutant, Mann et al., Cell 33:153–159 (1983). An MLV viral genome (with a single 350 bp deletion in the region bearing packaging sequences) was stably transfected into NIH3T3 cells. One of three lines recovered quickly reverted to replication competency. Another helper cell line, psi2, became a useful line despite its tendency to recombine and is still in use today. In addition to reversion of 'psi-minus' packaging mutant lines to the 'psi-plus' phenotype, the viral genome was also passively transferred by the viral particles, although at a much lower rate, psi2 was the prototype for more advanced packaging or helper cell lines, such as PA317 discussed in the Miller et al., U.S. Pat. No. 4,861,719 which contains additional mutations, making it more difficult for the cis and trans acting portions of the viral genome to recombine.

VL30 is naturally packaged and transmitted by psi2 cells, as well as by other MLV and primate retroviral virions. The VL30 used in present invention contains no known intact structural genes, but does contain psi-like sequences.

VL30s are not known to be oncogenic despite their close association with the highly oncogenic MLVs. Experimentally, MLVs have activated many tumors and permitted the isolation of various oncogenes, but there are no examples in which mouse VL30 genes have participated directly in oncogenesis. Similar rat VL30 elements have been shown to recombine with MLV during the genesis of Harvey and Kirsten MSV retroviruses (Ellis et al., Nature 292:506–511, 1981; Roop et al., Nature 323:822–824, 1986), which induce mouse epithelial tumors. Since mouse VL30 sequences are very actively transcribed under a variety of stimuli, they might act as insertional mutagens by gene activation, similar to murine retroviruses. Recently, the rat VL30 sequences in Harvey sarcoma virus were shown to enhance the transcriptional activity of the accompanying ras gene (Velu et al., J. Virology 63:1384–1392, 1989). In turn, coexpression of ras activates the transcription of murine VL30 (Owen et al., Mol. Cell Biol., 10:1–9, 1990). Despite their close association with oncogenic MLV viruses, VL30s have not been directly linked to any oncogene activation event, other than circumstantial examples such as those described above. Therefore, the VL30s are less likely to become involved in oncogenesis than MLV. This also explains why a large number of VL30s reside within the mouse genome, while germline MLVs are few. By remaining benign and not complicating the host organism with undue reverse transcription, oncogenicity, and translational burdens, VL30s and other retrotransposons have established a niche. Selfish DNA parasites appear to be tolerated by the host.

According to the present invention, transduction of foreign gene sequences into cells or organisms is made possible by insertion of the foreign gene sequences into a retrotransposon genome, and by transfection of the recombinant, transcriptionally active retrotransposon genome into cells capable of transmitting retrotransposon RNA or DNA, preferrably RNA (helper cells). The growth media of such cells contains infectious retrotransposon particles whose host range (range of infectively) is determined by the helper cells, and whose infectivity is usually limited to one round of replication. Once the retrotransposon particles or virions so generated have entered the recipient cells, the transposon RNA is reverse transcribed into DNA and is inserted into the genome of the recipient cell. A preparation of recipient cells containing the retrotransposon in high and usable yield is obtained by infecting additional recipient cells with additional, infectious virion particles.

The integrated retrotransposon can express either the LTR promoter transcriptional unit, and/or by an internal transcriptional unit if so equipped, as RNA and, preferably, as protein which results in a useful phenotype. The foreign genes can be transcribed from either promoter, or potentially from a third promoter. Furthermore, without expression retrotransposons can be used in this manner to mark a cell, species, or strain, in order to provide a unique identifying "fingerprint". The retrotransposon can additionally comprise genetic material which encodes at least one dominant selectable marker. Useful selectable markers include, for example, aminoglycoside phosphotransferase (nea, G418, APH), dihydrofolate reductase (DHFR), hygromycin-B-phosphotransferase (HPH), thymidine kinase (TK), xanthine-guanine phosphoribosyltransferase (XGPRT, gpt), chloramphenicol acetyltransferase (CAT), luciferase, and the like. Also, the retrotransposon can additionally comprise genetic material which encodes a peptide, antibody, antigen, hormone, or drug which is not normally expressed in the cell, organism, or species at biologically significant levels.

The main advantages of retrotransposons are that they are relatively nononcogenic and nonpathogenic. Aside from insertional mutagenesis, the specific vector VL30 has no known disease etiology or history of oncogenesis, having resided in the germline of mice for millions of years. Such long residence, together with evidence for recent insertion of a VL30 element into the Balb/c mouse genome (Courtney et al., J. Virol. 43:511–518, 1982) constitutes de facto evidence that VL30 is also a germline vector for transgenesis which is potentially stable for long time periods. VL30s bearing foreign genes are efficiently transmitted, and up to a hundred copies or more of a gene(s) can be inserted into a cell.

The present invention is potentially useful in human gene therapy, where rare oncogene activation events and recombinations due to MLV vector sequences can be avoided by substituting retrotransposon vectors.

The source of genetic material transmitted in such a retrotransposon vector can be from other organisms, clones, plasmids, and the like, or it may be synthetic. The invention may be used to modify a species or to create a new species. It is demonstrated herein that up to 50 or more copies can be inserted into the genome, permitting the opportunity to introduce many genes for the purpose of multi-trait introduction, or possibly for overexpression. Also, tandem integration may take place, and large RNA transcripts of these multimers may be made naturally. Thus, multiple cellular genetic elements can be introduced and expressed in tandem in RNA or as separate transcriptional units within a single cell or organism.

Silent VL30 transcriptional units exist, which can be used to switch VL30s off after just one round of replication due to the copying of the last LTR region during reverse transcription. A variety of VL30 LTRs are available, which contain control elements responsive to specific stimuli including: cellular transformation, glucocorticoids, activators of protein kinase C, serum (epidermal growth factor) stimulation, and the like. These can be tailored to meet the expression needs of individual applications. Since no essential structural genes appear to be present, it is demonstrated herein that it is possible to interrupt certain regions with foreign gene constructs without disrupting the ability to transpose effectively. In addition, many tools and methods of expression and vectorology used with retroviral vectors (such as deletion, double-expression, self-inactivation, germline insertion, and the like) are also possible with retrotransposons, since their mode of transmission and expression is similar. Existing cell lines such as psi2 and PA317 can be used to propagate VL30 much in the same way as retroviral vectors, the principal difference being the use of cellular "jumping gene" retrotransposons rather than the tumor viruses which have been used in such systems to date. Further, the use of various other types of retrotransposons will provide specialized attributes for highly specialized gene engineering.

INDUSTRIAL APPLICABILITY

Figure 1:
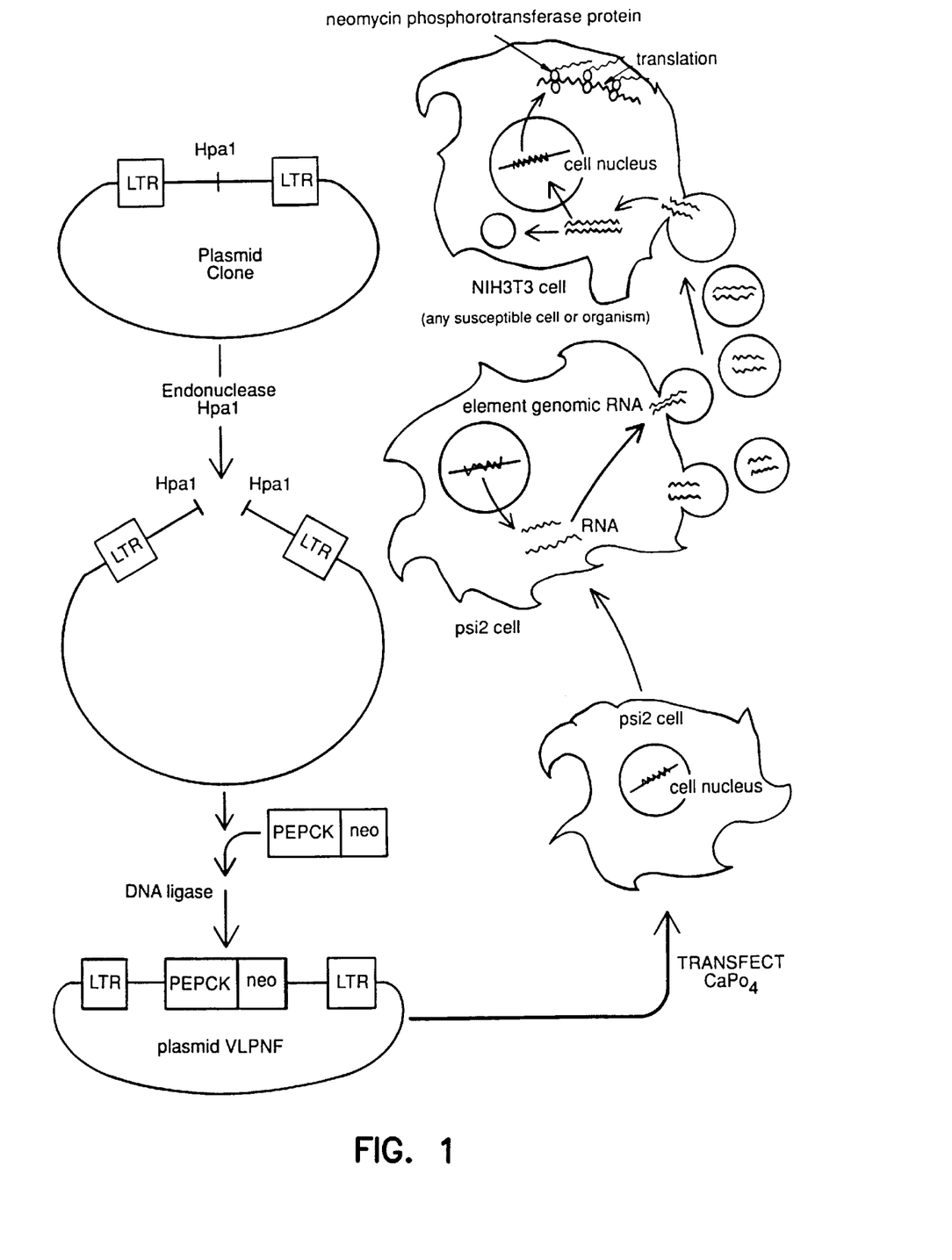
FIG. 1 is a schematic diagram of the invention showing the genesis of cells stably transduced by mobile element VLPNF.

FIG. 1 is a schematic diagram which generally shows the method of the present invention wherein cells are stably transduced by mobile element VLPNF. A plasmid clone of reverse transcribed VL30 element NVL3 was digested with restriction endonuclease Hpa1, and a blunt-end fragment bearing the rat cytosolic phosphoenolpyruvate carboxykinase [PEPCK] promoter and bacterial neo gene was ligated into the restriction site. The plasmid was transfected into psi2 cells which contain retroviral helper functions (core proteins, polymeraseintegrase, and envelope glycoprotein). The VLPNF-psi2 cells produced particles bearing RNA copies of the chimeric mobile element VLPNF, which are able to infect cells with high efficiency. Once inside the recipient cell, the RNA was reverse transcribed into DNA, and integrated into cell DNA, where it was expressed as RNA, and as protein expressing the neo phenotype. A variation involves the use of replication competent virus in place of helper cells.

According to the method of the present invention, a foreign gene promoter, PEPCK from the rat, together with a bacterial neomycin resistance gene (neo) was inserted into a VL30 genome in various orientations. These constructs were transfected into helper (psi2) cells. It is within the contemplated scope of the present invention that any other replication competent virus or helper cell line can be used in the place of the donor helper cells. From these cells, VL30 efficiently transferred the foreign genes to NIH3T3 cells (titre $10^{3-4}$). It is within the intended scope of the present invention that titre can be increased by such methods as centrifugation, concentrating cartridges, use of polybrene, and the like. It is also within the contemplated scope of the present invention that any susceptible cell or organism can be used as recipient cells. The VL30 genes were expressed as both RNA and as a protein, which they conferred with a selectable phenotype (G418 resistance) upon the recipient cells. It is also within the contemplated scope of the present invention that any suitable dominant selectable marker or phenotypic selection technique may be encoded with the retrotransposon.

A nonpermuted plasmid clone carrying the mouse VL30 retrotransposon genome was digested with restriction endonuclease Hpal, and was ligated to a recombinant DNA construct consisting of the rat nuclear phosphoenolpyruvate carboxykinase [PEPCK] promoter, region extending from 355 base pairs before the start site of transcription to 73 base pairs after the start site, followed by the entire bacterial neomycin phosphotransferase gene, without polyadenylation signal. Two clones were recovered which corresponded to both (forward and reverse) orientations of the chimeric DNA construct, henceforth called VLPNF (forward) and VLPNR (reverse), respectively. The chimeric retrotransposonPEPCKneo constructs were grown in prokaryotic plasmid vector, pGEM3, after transfection of the DNA ligation mix into E. coli competent cells. The plasmid DNA was harvested, and was transfected by the calcium phosphate method (Graham et al., Virol. 52:456–467 (1973), into psi2 helper cells (Mann, et al., supra., 1983). After one day, 200 µg/ml of the drug G418 was added and growth of psi2 cells on the selective media continued for ten additional days. Mass cultures of G418 surviving cells were grown in media without G418, and purified media from rapidly growing psi2 cells was used to transduce VL30 retrotransposons into such recipient cells as NIH3T3 cells, PA317 cells, and chicken embryo fibroblasts. Reverse transcriptase assay was used to ascertain the presence or absence of helper virus in donor and recipient clones. DNA blotting (Southern blots), and RNA blotting (Northern blots) were used (described in Maniatis et. al., 1984, "Molecular Cloning", Cold Spring Harbor Laboratory, 1982) to determine the identity and expression, respectively, of the inserted sequences. S1 nuclease analysis (Berk et al., cite needed) was used to determine the start site of transcription of the internal transcriptional cassette. Reverse transcriptase assay (Goff et al., J. Virol., 38:239–248, 1981) was used to determine whether cells were producing infectious virus capable of reverse transcribing RNA.

After incubating NIH3T3 cells with media from psi2 cells expressing neo resistance after transfection with the VLPN vectors, NIH3T3 cells were themselves selected in G418 to see whether the selectable neo gene was transduced by the particles.

Tables IA and IB below show experiments which were performed to titre the transducing power of the particles in the media. In Table IA VLPNF and VLPNR constructs were transfected into psi2 cells and the viral supernate from psi2 clones was titred on NIH3T3 cells and were selected for ten days with G418.

TABLE IA

TITRE OF VLPN RETROTRANSPOSONS

| PSI2-NIH3T3: contruct | $10^0$ | $10^{-1}$ | $10^{-2}$ | $10^{-3}$ | $10^{-4}$ |
|---|---|---|---|---|---|
| VLPNF | + | + | + | +(52) | – |
| VLPNR | + | + | +(20) | – | – |

In Table IB, the viral filtrate PA317 viral helper cells transduced with VLPNF from psi2 cells were cloned after selection with G418, and media from these cells was used to transduce chick embryo fibroblasts (CEF) either undiluted, or 10,000 fold diluted. Three clones of PA317 produced a titre of $10^4$ infectious units per ml, or greater.

TABLE IB

| PA317-CEF: clone: | $10^0$ | $10^{-4}$ |
|---|---|---|
| PA317 | – | |
| CEF | – | |
| 2S | + | |
| 2V | + | |
| 2Y | + | + |
| 3B | + | |
| 2B | + | |
| 2E | + | + |
| 2G | + | |
| 2L | + | + |
| 2J | + | |
| 2N | + | |
| 1B | + | |
| 1C | + | |
| Uncloned | + | |

This experiment shows that VLPNF transduced cells when diluted a thousand fold ($\geq 10^3$ transducing units per ml), whereas VLPNR transformed at a hundred fold dilution, but not a thousand fold.

Figure 2A:
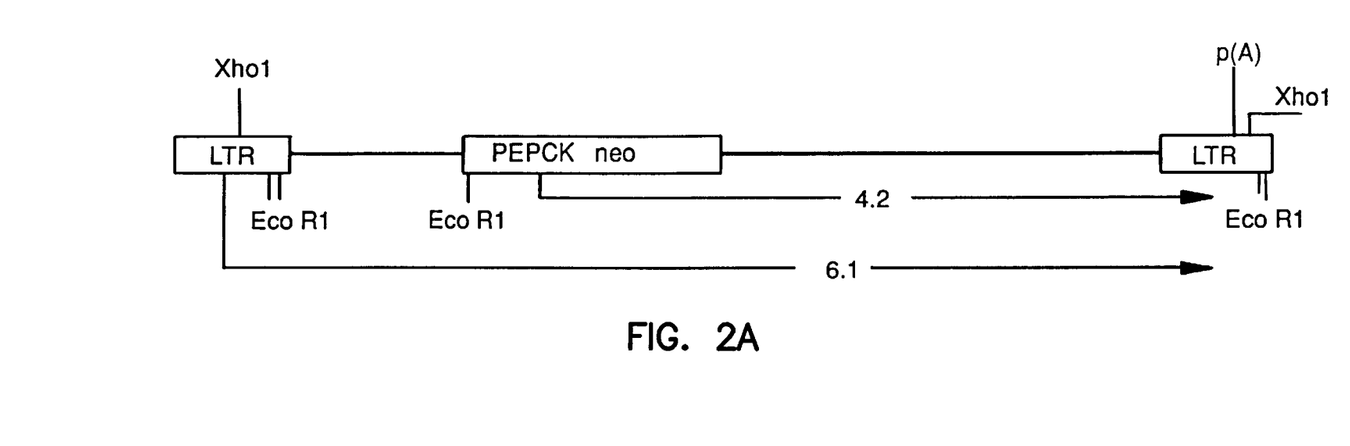
FIGS. 2a and 2b are restriction maps depicting gene transfer with retrotransposon VL30 in (a) construct pVLPNF; and (b) construct pVLPNR.
Figure 2B:
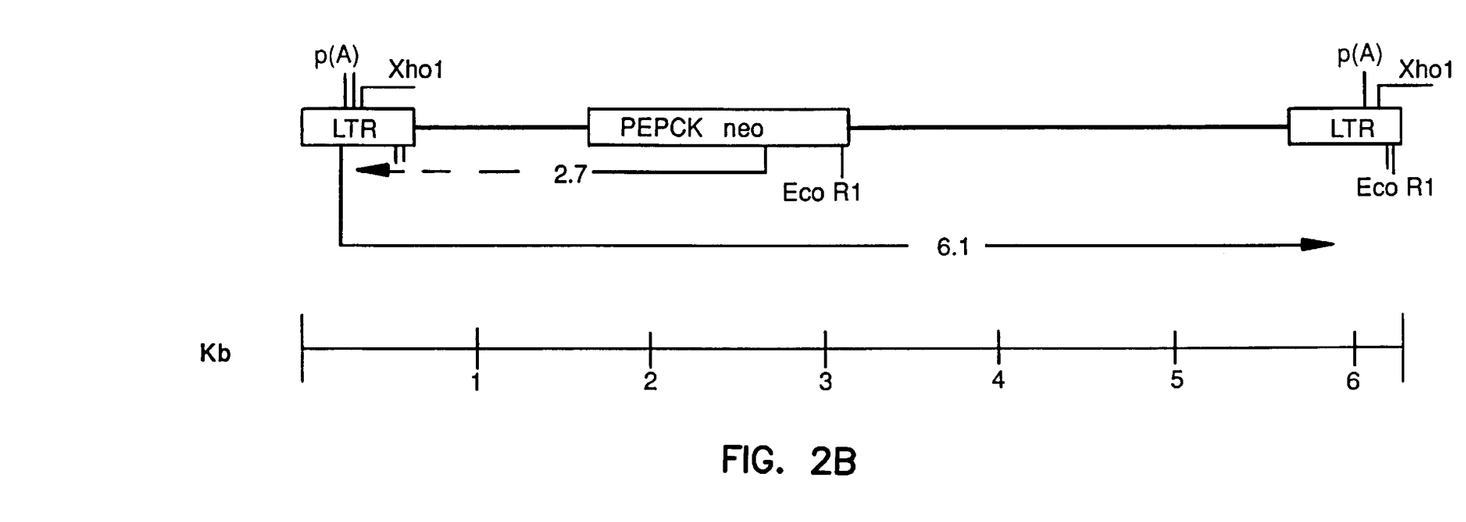

Clones of cells from the dilutions were isolated by preparing cells from the colonies which formed. RNA and DNA from the recipient cells were examined by electrophoresis and the blotting methods described above. When hybridized to the bacterial neo gene, isolated from a gel, two RNA transcripts were clearly visable at about 6 kilobases and 4 kilobases, the sizes predicted from the map of the VLPN clones, as seen in FIGS. 2a and 2b. The larger size transcript corresponds in size to the full-length VL30 genomic RNA transcript, while the smaller transcript is the size expected from the PEPCKneo internal transcriptional unit of clone VLPNF. VLPNR mass cultures and clones revealed only a light smear, suggesting possible heterogeneity from the internal promoter, with no clear VL30 transcript visable. DNA blots of cell clones infected with the two constructs revealed EcoR1 restriction endonuclease fragments of the sizes expected, as seen in FIGS. 2a and 2b, except that the mass cultures and a clone from VLPNF also bore other fragments suggestive of multiple and/or rearranged copies of the neo containing sequences. Since the VLPNR clone has a reversed transcriptional unit which should be capable of making an RNA in the negative sense relative to the retrotransposon RNA, some transcriptional interference is expected which should result in rearrangements, deletions, and changes in transcription (Hodgson et al., unpublished results using avian leukosis virus). In addition, since there is no polyadenylation signal known in the reverse VLPNR chimera, it is not possible to tell where the internal neo transcript will terminate. However, selectability of the sequences indicates that some transcription does take place. VLPNR serves as a control for forward VLPNF experiments.

Figure 3A:
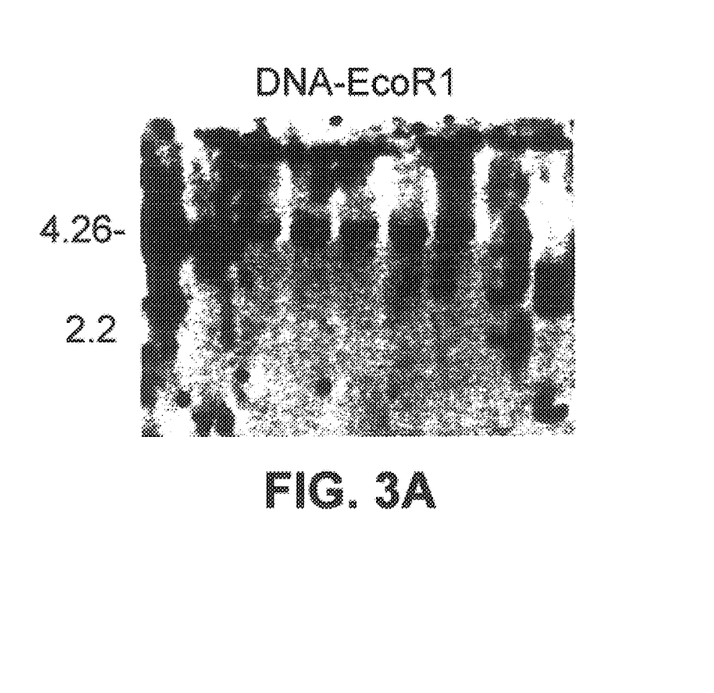
FIGS. 3a and 3b are photographs depicting: (a) Southern blot showing DNA of mass cultures, lane 1, and individual clones of VLPN vectors transduced into NIH3T3 cells, digested with Eco R1 and hybridized to $^{32}$P-radiolabelled neo sequences; (lane 1 mass culture; 2–7 clones, VLPNF; 8 VLPNR mass culture; lane 9 VLPNR clone); and, (b) Northern blot analysis of VLPN-transduced NIH3T3 cells, showing presumptive VL30 and PEPCK neo RNA bands; (lane 1–2, VLPNF mass culture; lanes 3–4, 5–6, 7–8, VLPNF clones (two lanes each); 9–10, VLPNR clone).
Figure 3B:
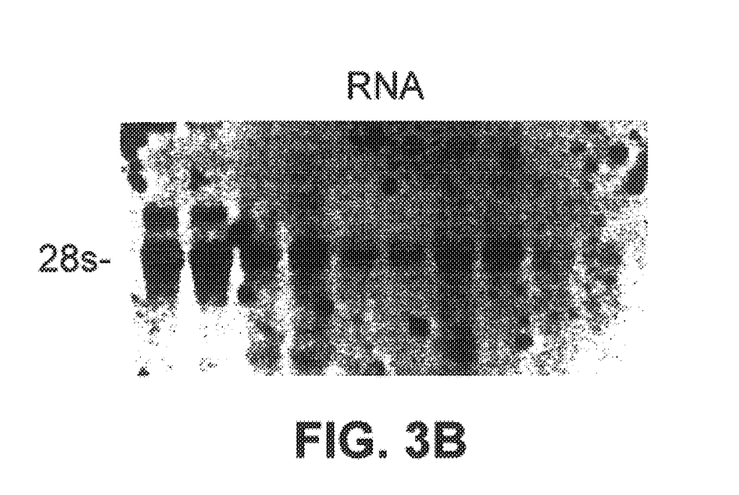

The mass cultures of VLPNF-psi2 producer cells were used to transduce the amphotropic producer cell line PA317, which is another helper cell line with a greatly expanded range of infectable host cells, including human cells. In order to see if multiple VL30s could be transduced, PA317s were exposed to multiple doses of media from the psi2 cells, which can repeatedly infect PA317s due to the different tropisms of the two types of cells. Clones of PA317s were then isolated, and RNA and DNA from these lines were examined. DNA from mass cultures and clones of cells transduced with VLPNF were digested with XhoI (see FIG. 2a), which releases the internal neo-containing fragment. It is clear from the blot that all cells were transduced at least once, but that a large number were repeatedly transduced, and that multiple species of VL30 were transduced repeatedly from the psi2 producers. From visual and digitized densitometric analysis of these films, it is estimated that the PA317 cells were transduced with from one to about 50–100 copies during the repeated bombardment. Some neo-containing transductants were recovered which bore deleted, smaller sized inserts than expected, indicating that some material had been rearranged. Nevertheless, these cells which bore single copies of such material also expressed the neo phenotype (G418 resistance), showing that a functional neo gene remained. It is clear from examination of the blots shown in FIGS. 3a and 3b, however, that most of the VL30 retrotransposons which were transferred did contain near full-length VLPN DNA. Therefore, rearrangement is a possible but not probable event. The repeated insertion of variants of the same approximate size suggested that clones of psi2 cells in the producer mass cultures were repeatedly producing the characteristic rearrangements which were observed. Conversely, some of the same clones may have been repeatedly isolated. Since the DNA had been transfected into the psi2 cells, rearrangement could have taken place during the transfection process which carried over during transduction.

Comparison of the DNA blots with RNA blots revealed that expression also characterizes certain types of insertion observed in the DNA blots. First, bands of approximately 6–7 kb on the RNA blots mark the approximate position expected for genomic VL30 transcripts, while higher bands are not characteristic and are not expected. Measured sizes of approximately 13 and 19kb for these larger transcripts are about the sizes expected if multimeric, tandem insertions of VL30 had occurred, which could be transcribed in tandem. If this were the case, multimeric transcripts should only be observed in those samples in which multiple transductions had occurred. Since this is the case (see apparent single copy sequences: 2k, 2l, 2m, 2n, 2o, 2t, 2v, 2y, 3a, 1a, 2d, 2e, bearing only unique genome sizes of RNA, versus clones with multiple inserts bearing apparent multimeric transcripts), it is speculated that tandem integration took place, and that RNA transcripts larger than one genomes length were made therefrom. It was also determined whether multiple insertions of VLPNF would result in elevated levels of expression, or whether the presence of additional cis-acting control regions in the genomic DNA of these cells would dilute the available supply of transcription factors. Presumably each chromosomal locus has its own particular effects upon gene expression, so a variability of results was expected. However, when the levels of transcription were compared on the basis of measured copy number, an inverse effect was noted suggesting that additional copies of VLPNF did not necessarily result in an increased expression. Another interpretation is that since selection pressure was applied, clones were selected in which those with only one copy were also sufficiently expressed to survive along with those with multiple copies, some of which might have been silent. Therefore, it is not yet clear whether overexpression from the VL30 LTR is possible by inserting multiple copies with a given insert.

Figure 4A:
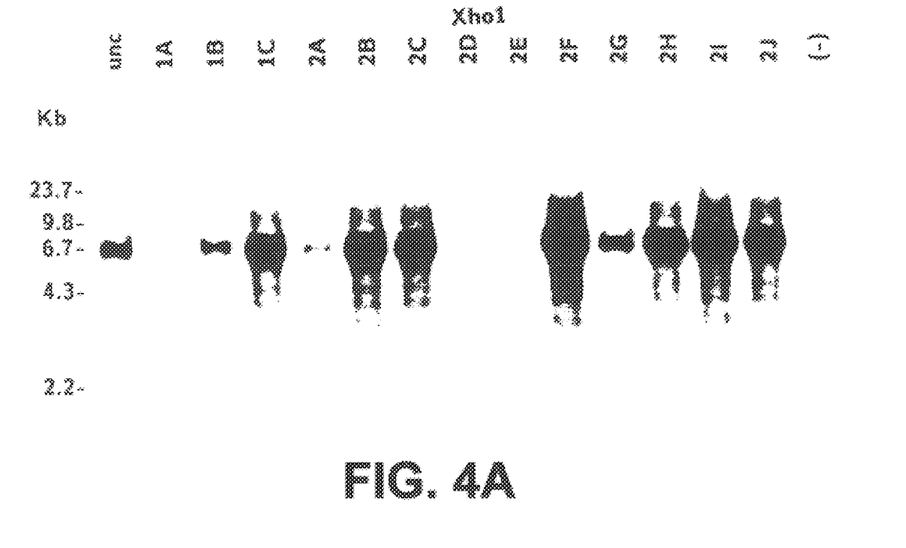
FIGS. 4a and 4b are photographs depicting PA317 cell clones transduced with VLPNF: (a) Southern blot of PA317 DNA digested with XhoI and hybridized to $^{32}$P-radiolabelled neo sequences; and, (b) total RNA blots from the clones, hybridized to neo.
Figure 4B:
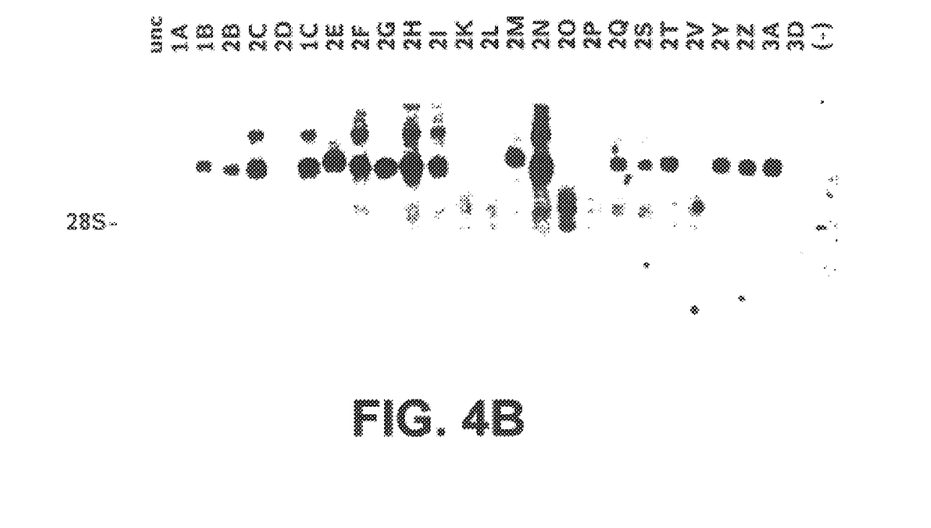

From an analysis of the sizes of DNA fragments observed (as shown in FIG. 4a), it is seen that the same size mutants are present in a number of diverse cell lines, suggesting a common parentage. This implies that the mutations may have occurred prior to generation of the RNA, and not during the present infection. This, together with the data showing that most of the XhoI fragments (including all of the internal VLPN-PEPCK neo material) were intact in most inserts passaged by VL30 retrotransposons, suggests that VL30 is rather stable and able to pass intact material. Some instability is characteristic of all reverse-transcribed material, and this was also observed. Since mouse cells contain many copies of VL30, including several transcriptionally active VL30s, these vectors were undoubtedly not the only VL30 material being passaged (Hatzoglou et al., 1991, in press, Human Gene Therapy) by psi2 cells. Hence, the hydridization probe used in these studies was derived only from the chimeric bacterial portion of the insert which is not present in any natural VL30, or in these cells (see negative control PA317).

The data shown herein with VL30 together with other data not shown clearly reveal high levels of expression from the LTR promoter, as well as selectable levels of expression from the internal promoter. Both promoters can be used to express the foreign gene sequences.

Thus, VL30 vectors can be used with already developed helper cell lines such as psi2 and PA317. VL30 maintains the integrity of the foreign genes and is capable of delivery of individual, or large numbers (>50) of copies of the foreign genes, easily manipulated in the laboratory.

The present invention also contemplates the selection for high levels of expression, concentration of VL30 particles to obtain higher titre, multiple inserts, deletion mutagenesis to determine which sequences can be used to modify or to improve the system for gene transfer and the like. Also, vectors can be built in which the second generation VL30 transcriptional unit is transcriptionally silent, allowing center-stage to the inserted transcriptional unit, and reducing the chance that VL30 would be transmitted during a secondary infection of the host with another retrovirus.

Virtually all the techniques used to improve retroviruses can also be applied to VL30. VL30 size permits up to 5 kb of genetic information to be inserted without the need for deleting any VL30 information (MLV particles package up to about 10 kb of genetic information in duplicate). In addition, other types of retrotransposon may be utilized in a similar manner as VL30. It is recognized, however, that some systems necessitate different helper mechanisms than those used for the elements described here.

As discussed above, it is expected that many types of genes will be appropriate for use with a retrotransposon vector. Moreover, it is expected that other types of retrotransposons will provide suitable as vectors. Also, the selection of a preferred host is not meant to be limiting, and many other hosts may prove acceptable. As such, while the present invention has been described in conjunction with a preferred embodiment and illustrative examples, one of ordinary skill after reading the foregoing specification will be able to affect various changes, substitutions or equivalents, and alterations to the compositions and methods set forth herein. It is therefore intended that the protection granted by the Letters Patent hereon be limited only by the definitions contained in the appended claims and equivalents thereof.

I claim:

1. A biologically active transduction vector incorporating no viral structural genes comprising:

(a) at least two long terminal repeat (LTR) sequences isolated from a mammalian retrotransposon;

(b) a mammalian retrotransposon packaging signal; and (c) a foreign gene.

2. The vector of claim 1, wherein the packaging signal is from a rodent VL30 retrotransposon.

3. The vector of claim 1, wherein the retrotransposon is a rodent VL30 retrotransposon.

4. The vector of claim 1, wherein the vector further comprises a second transcriptional control region operably linked to the foreign gene.

5. The vector of claim 1 in which the foreign gene is selected from the group consisting of aminoglycoside phosphotransferase, dihydrofolate reductase, hygromycin-β-phosphotransferase, thymidine kinase, xanthine-guanine phosphoribosyltransferase, chloramphenicol acetyltransferase, and luciferase.

6. The vector of claim 1 in which sequences in the long terminal repeat are responsive to glucocorticoids, activators of protein kinase C, serum growth factor stimulation (epidermal growth factor), or phorbol esters (TPA).

7. The vector of claim 1 in which the foreign gene encodes a peptide, antibody, antigen, hormone, RNA molecule or drug not normally expressed in the cell, at biologically significant levels.

8. A recombinant virus comprising the vector of claim 1.

9. An isolated host cell comprising the vector of claim 1.

* * * * *

UNITED STATES PATENT AND TRADEMARK OFFICE
CERTIFICATE OF CORRECTION

PATENT NO.: 5,879,933
DATED: March 9, 1999
INVENTOR(S): Hodgson

It is certified that error appears in the above-identified patent and that said Letters Patent is hereby corrected as shown below:

On the front page, section [54], delete "Mammalian Retrotransposons" and insert --Method of Gene Transfer Using Retrotransposons-- therefor.

Signed and Sealed this

Seventeenth Day of April, 2001

Attest:

NICHOLAS P. GODICI

Attesting Officer

Acting Director of the United States Patent and Trademark Office